(12) United States Patent
Geissler et al.

(10) Patent No.: US 6,500,956 B1
(45) Date of Patent: Dec. 31, 2002

(54) METHOD FOR THE CATALYTIC PRODUCTION OF SUBSTITUTED BIPYRIDYL DERIVATIVES

(75) Inventors: Holger Geissler, Mainz (DE); Peter Gross, Kelsterbach (DE)

(73) Assignee: Axiva GmbH (DE)

( * ) Notice: Subject to any disclaimer, the term of this patent is extended or adjusted under 35 U.S.C. 154(b) by 0 days.

(21) Appl. No.: 09/674,063

(22) PCT Filed: Apr. 24, 1999

(86) PCT No.: PCT/EP99/02788

§ 371 (c)(1),
(2), (4) Date: Nov. 30, 2000

(87) PCT Pub. No.: WO99/55675

PCT Pub. Date: Nov. 4, 1999

(30) Foreign Application Priority Data

Apr. 29, 1998 (DE) ......................... 198 19 010

(51) Int. Cl.⁷ ............................. C07D 401/02
(52) U.S. Cl. ...................... 546/257; 546/255
(58) Field of Search ................. 546/255, 257

(56) References Cited

FOREIGN PATENT DOCUMENTS

| EP | 206 543 | 12/1986 |
|---|---|---|
| GB | 1 340 006 | 12/1973 |

*Primary Examiner*—Zinna Northington Davis
(74) *Attorney, Agent, or Firm*—Connolly Bove Lodge & Hutz LLP

(57) ABSTRACT

The invention relates to a process for the preparation of bipyridyls by converting at least one pyridine of the formula (III)

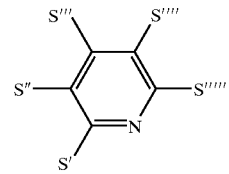

(III)

in which

S', S'', S''', S'''' and S''''', independently of one another, are identical or different and are hydrogen, $(C_1-C_{18})$-alkyl, alkoxy-$(C_1-C_{18})$, acyloxy-$(C_1-C_{18})$, aryloxy-$(C_1-C_{18})$, perfluoroacyloxy-$(C_1-C_8)$, $NO_2$, $(C_1-C_{18})$-aryl, $(C_1-C_{18})$-heteroaryl, halogen, hydroxyl, nitro, nitroso, CN, COOH, CHO, $PO_3H_2$, $SO_3H$, $SO_2R$, SOR, $NH_2$, NH-alkyl-$(C_1-C_{18})$, N-alkyl$_2$-$(C_1-C_{18})$, protected amine, $CF_3$, NHCO-alkyl-$(C_1-C_4)$, N-alkyl-$(C_1-C_4)$-CO-alkyl-$(C_1-C_4)$, COO-alkyl-$(C_1-C_{18})$, $CONH_2$, CO-alkyl-$(C_1-C_{18})$, NHCOH, NHCOO-alkyl-$(C_1-C_4)$, CO-$(C_1-C_{18})$-aryl, COO-$(C_1-C_{18})$-aryl, CHCH-$CO_2$-alkyl-$(C_1-C_{18})$, $CHCHCO_2H$, PO-phenyl$_2$, PO-alkyl$_2$-$(C_1-C_4)$, $(COO^-)_n(\text{cation})^{n+}$, $(PO_3^{2-})_n(\text{cation})_2^{n+}$, $(SO_3^-)_n(\text{cation})^{n+}$ and/or $(O^-)_n(\text{cation})^{n+}$, where optionally S', S'', S''', S'''' and/or S''''' among one another together form one or more aliphatic and/or aromatic rings and/or in which optionally S', S'', S''', S''''and/or S''''' forms a bridge to at least one further pyridine of the formula (III)

and/or in which optionally the radicals S', S'', S''', S'''', and/or S''''' have the meanings given above and are substituted by at least one radical which has the meaning given above for S', S'', S''', S'''' and/or S''''' in water in the presence of an alcohol, a base, a palladium catalyst and optionally one or more further solvents at a temperature of 0–200° C.

30 Claims, No Drawings

METHOD FOR THE CATALYTIC PRODUCTION OF SUBSTITUTED BIPYRIDYL DERIVATIVES

This application is a 371 of PCT/EP99/02788 filed Apr. 24, 1988.

The present invention relates to an improved process for the catalytic preparation of substituted bipyridyl derivatives by converting substituted halopyridine derivatives with a base and a reducing agent in the presence of a palladium catalyst.

Such a process, which for bipyridyls follows the reaction equation

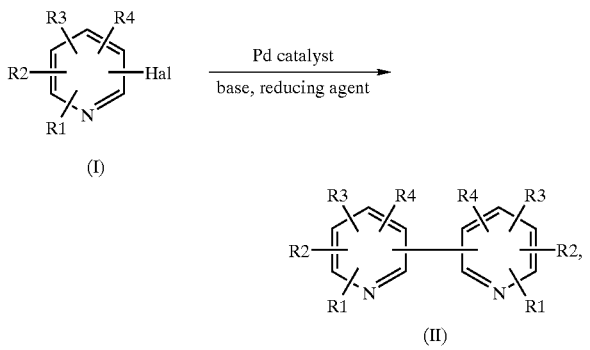

has been described in the publications listed below, the reaction with chloropyridines frequently resulting in low yields, and the use of bromopyridines and iodopyridines, which are significantly more expensive and therefore of lesser interest industrially, resulting in higher yields. The processes known hitherto have cost and/or ecological disadvantages.

Bipyridyls, which are also frequently referred to in the literature as bipyridines, including their derivatives are, for example, important as industrial and medicinal intermediates, as analytical reagents or as ligands for the synthesis of metal complexes having catalytic activity. The use of bipyridyl metal complexes, particularly of ruthenium complexes, is of particular importance due to the use as photosensitizers for sensitizing semiconductor surfaces, as photocatalysts for solar cells, in particular for photovoltaic cells or photoelectrochemical cells, as described, for example, in WO 91/16719 or EP-A-0 333 641, and for photo-induced electrolysis.

The synthesis of substituted bipyridyls from halopyridines usually only takes place with good yields in accordance with the prior art if stoichiometric amounts of a metal compound are used. If catalytic amounts of these metal compounds are used, the yield is, by contrast, low in most cases, and the bromopyridines or iodopyridines are used as initiator materials.

Tiecco and Testaferri describe, in Synthesis 1984, 736 et seq., the synthesis of bipyridyl derivatives using stoichiometric amounts of elemental zinc and nickel chloride and four equivalents of triphenylphosphine in dimethylformamide as solvent at 50° C. Using this process, it is possible, for example, to convert 3-bromo-2-methoxypyridine in a yield of 75% with one equivalent of zinc(II) chloride and one equivalent of nickel(II) chloride as byproduct. In two comparative experiments, in which palladium on activated carbon is used as catalyst, or copper, the product 3,3'-dimethoxy-2,2'-bipyridyl can only be obtained in a yield of 18% or 23%; the experimental conditions are described in Synthesis 1978, 537 et seq. If catalytic amounts of nickel(II) chloride are used, as published by Zembayashi et al. in Tetrahedron Lett. 1977, 4089 et seq., the dehalogenated initiator material is primarily obtained, and the desired product is obtained only in a low yield.

Using the process described by Tiecco and Testaferri it is also possible to convert chloropyridines, although large amounts of heavy metal salts are also produced at the same time, making this process neither ecologically nor economically attractive. For example, 2-chloro-5-methoxypyridine is converted in a yield of 88% to 5,5'-dimethoxy-3,3'-bipyridyl with one equivalent of zinc(II) chloride and one equivalent of nickel(II) chloride as byproduct.

In DE-A-39 21 025, Langhals discloses that the reaction described by Tiecco and Testaferri can also be carried out in the presence of free phenolic hydroxyl groups. At the same time Langhals discloses that the zinc hydroxide produced in the reaction as a byproduct can only be separated off with difficulty in the examples for the synthesis of 3,3'-dihydroxy-2,2'-bipyridyl and 3,3'-dihydroxy-2,2'-biquinoline.

Newcame discloses, in J. Inorg. Nucl. Chem. 1981, Vol. 43, 1529 et seq., the conversion of methyl-substituted bromopicoline to the corresponding bipyridyl with catalysis by palladium on activated carbon and a phase-transfer reagent in the presence of sodium formate as reducing agent in a two-phase system. Using this process, for example, 2-bromo-6-methylpyridine (=2-bromo-6-picoline) can be converted in a yield of 59% to 3,3'-dimethyl-2,2'-bipyridyl. The disadvantage of this method is that it is absolutely obligatory to use a phase-transfer reagent as cocatalyst in addition to palladium. Likewise, only bromopyridines which are usually substituted by alkyl groups are usually used as initiator materials for this method.

The classical Ullmann reaction, as described by Fanta in Synthesis 1974, 9 et seq., requires extremely drastic reaction conditions and the use of stoichiometric amounts of copper as reducing agent. In most cases, it produces only low yields of the desired bipyridyls or of derivatives thereof.

According to Fanta, the Ullmann reaction cannot be used for the synthesis of bipyridyls which are substituted by amino, hydroxyl and/or free carboxyl groups.

The synthesis of carboxy-substituted bipyridyls of the formula (IIa)

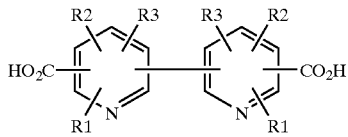

currently represents a particular problem. This class of substance is usually obtained by oxidation of the readily accessible dimethyl-substituted bipyridyls with potassium permanganate, as is described, for example, by Bruce in Liquid Crystals, 1996, Vol. 20, pages 183–193.

In DE-A-24 50 100, Shaw discloses that bipyridyls and bipyridyls substituted by alkyl, amino, cyano and/or carboxyl groups can also be made accessible from the corresponding pyridines in yields of only 50% by an electrochemical process. The large number of byproducts prevents an industrial and ecologically and economically attractive realization. Shaw discloses at the same time that in the case of the other known processes for the preparation of bipyridyls, metal derivatives of pyridine, especially sodium derivatives, frequently have to be prepared as intermediates, meaning that the preparation of bipyridyls by such processes is hazardous and relatively expensive.

In J. Chem. Soc. 1956, 616 et seq., Badger and Sasse describe the conversion of 50 g of nicotinic acid with activated nickel prepared from 125 g of nickel alloy to only 1 g of the coupled product. The low yield of this process renders the process uninteresting for the synthesis of this class of substance.

U.S. Pat. No. 3,767,652 teaches that 2,2'-bis(3-pyridinols) can be prepared in low yields up to 35% by oxidative coupling of the corresponding pyridinols with stoichiometric amounts of lead dioxide as oxidizing agent. The use of stoichiometric amounts of lead salts renders this process ecologically unacceptable.

The synthesis of bipyridyls without substituents takes place, according to DE-A-22 30 562, with yields up to 65% by converting chloro- or bromopyridine in methanol in the presence of water, an additive which has a reducing action, such as, for example, hydroxylamine or hydrazine, a base, such as, for example, potassium hydroxide, and supported palladium. The synthesis of bipyridyls containing alkyl groups as substituents, which are referred to in the laid-open specification as inert substituents, was possible, however, only in yields of up to 26% in accordance with the process described. The great disadvantage of the process is the high conversion to dehalogenated pyridines, which can amount to 68%. The dehalogenation appears to be favored by large amounts of water in the reaction medium.

EP-A-0 206 543 discloses the synthesis of bipyridyl by converting a halopyridine in the presence of 0.2 to 3 MPa of carbon monoxide, an alkaline medium and a supported palladium catalyst. The use of carbon monoxide is, however, uneconomical for industrial realization in view of the high safety requirements for handling this highly toxic gas.

Since the processes for the synthesis of substituted bipyridyls hitherto described can only be carried out in good yields with a high ecological impact, there was a great need for a process which makes accessible substituted bipyridyls and, in particular, carboxy-substituted bipyridyls in a high yield and purity in a manner which is ecological and simple to carry out on an industrial scale. The object was to develop such a process.

This object is achieved by a process for the preparation of bipyridyls by converting at least one pyridine of the formula (III)

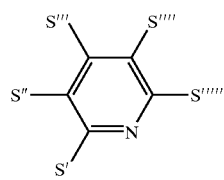

(III)

in which

S', S", S"', S"" and S""', independently of one another, are identical or different and are hydrogen, $(C_1-C_{18})$-alkyl, alkoxy-$(C_1-C_{18})$, acyloxy-$(C_1-C_{18})$, aryloxy-$(C_1-C_{18})$, perfluoroacyloxy-$(C_1-C_8)$, $NO_2$, $(C_1-C_{18})$-aryl, $(C_1-C_{18})$-heteroaryl, halogen, hydroxyl, nitro, nitroso, CN, COOH, CHO, $PO_3H_2$, $SO_3H$, $SO_2R$, SOR, $NH_2$, NH-alkyl-$(C_1-C_{18})$, N-alkyl$_2$-$(C_1-C_{18})$, protected amine, $CF_3$, NHCO-alkyl-$(C_1-C_4)$, N-alkyl-$(C_1-C_4)$-CO-alkyl-$(C_1-C_4)$, COO-alkyl-$(C_1-C_{18})$, $CONH_2$, CO-alkyl-$(C_1-C_{18})$, NHCOH, NHCOO-alkyl-$(C_1-C_4)$, CO-$(C_1-C_{18})$-aryl, COO-$(C_1-C_{18})$-aryl, CHCH-$CO_2$-alkyl-$(C_1-C_{18})$, $CHCHCO_2H$, PO-phenyl$_2$, PO-alkyl$_2$-$(C_1-C_4)$, $(COO^-)_n(\text{cation})^{n+}$, $(PO_3^{2-})_n(\text{cation})_2^{n+}$, $(SO_3^+)_n(\text{cation})^{n+}$ and/or $(O^-)_n$ $(\text{cation})^{n+}$, where the cation is an alkali metal (Li, Na, K, Rb, Cs), an alkaline earth metal (Be, Mg, Ca, Sr, Ba), $NR_2H_2$, $NR_3H$, $NRH_3$, $NR_4$, $NH_4$, $PR_2H_2$, $PR_3H$, $PRH_3$, $PR_4$ and/or $PH_4$ and where R, independently of one another, are identical or different and are $(C_1-C_{18})$-aryl and/or $(C_1-C_{18})$-alkyl, and where at least one of the substituents of S', S", S"', S"" and S""' is chloride, bromide or iodide, where optionally S', S", S"', S"" and/or S""' among one another together form one or more aliphatic and/or aromatic rings and/or in which optionally S', S", S"', S"" and/or S""' forms a bridge to at least one further pyridine of the formula (III)

and/or in which optionally the radicals S', S", S"', S"" and/or S""' have the meanings given above and are substituted by at least one radical which has the meaning given above for S', S", S"', S"" and/or S""' in water in the presence of an alcohol, a base, a palladium catalyst and optionally one or more further solvents at a temperature of 0–200° C.

Particularly preferably S', S", S"', S"" and S""', independently of one another, are identical or different and are hydrogen, methyl, ethyl, isopropyl, methoxy, acetoxy, trifluoroacetoxy, trifluoromethyl, O-phenyl, phenyl, fluorine, OH, nitro, nitroso, $NO_2$, CN, COOH, CHO, $PO_3H_2$, $SO_3H$, $NH_2$, NH-alkyl-$(C_1-C_8)$, N-alkyl$_2$-$(C_1-C_8)$, NHCO-alkyl-$(C_1-C_4)$, N-alkyl-$(C_1-C_4)$-CO-alkyl-$(C_1-C_4)$, $CONH_2$, CO-alkyl-$(C_1-C_8)$, NHCOH, CO-phenyl, $CHCHCO_2H$, PO-phenyl$_2$, PO-alkyl$_2$-$(C_1-C_4)$, $(COO^-)_n$ $(\text{cation})^{n+}$, $(PO_3^{2-})_n(\text{cation})_2^{n+}$, $(SO_3^-)_n(\text{cation})^{n+}$ and/or $(O^-)_n(\text{cation})^{n+}$, where the cation is Na, K, $NR_4$ and/or $PR_4$ and where R, independently of one another, are identical or different and are $(C_1-C_{18})$-aryl and/or $(C_1-C_{18})$-alkyl and where at least one of the substituents of S', S", S"', S"" and S""' is a non-inert substituent such as OH, COOH, $PO_3H_2$ or $SO_3H$, $(COO^-)_n(\text{cation})^{n+}$, $(PO_3^{2-})_n$ $(\text{cation})_2^{n+}$, $(SO_3^-)_n(\text{cation})^{n+}$ and/or $(O^-)_n(\text{cation})^{n+}$, where the cation is Na, K, $NR_4$ and/or $PR_4$ and where R, independently of one another, are identical or different and are $(C_1-C_{18})$-aryl and/or $(C_1-C_{18})$-alkyl, and where at least one of the substituents of S', S", S"', S"" and S""' is chlorine, bromine or iodine, where optionally S', S", S"', S"" and/or S""' among one another together form one or more aliphatic and/or aromatic rings and/or in which optionally S', S", S"', S"" and/or S""' forms a bridge to at least one further pyridine of the formula (III)

and/or in which optionally the radicals S', S", S"', S"" and/or S""' have the meanings given above and are substituted by at least one radical which has the meaning given above for S', S", S"', S"" and/or S""'.

The process is highly suitable for the preparation of symmetrical 2,2'-bipyridyls of the formula (IV), symmetrical 3,3'-bipyridyls of the formula (V) or symmetrical 4,4'-bipyridyls of the formula (VI),

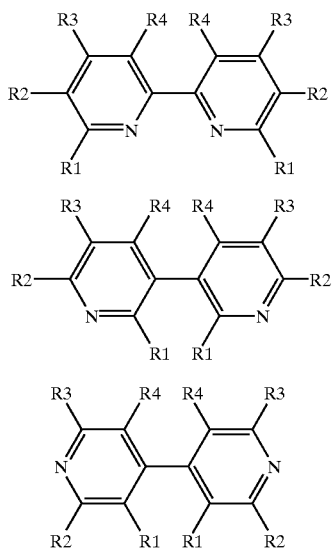

in which

R1 to R4, independently of one another, are hydrogen, ($C_1$–$C_{18}$)-alkyl, alkoxy-($C_1$–$C_{18}$), acyloxy-($C_1$–$C_{18}$), aryloxy-($C_1$–$C_{18}$), ($C_1$–$C_{18}$)-aryl, ($C_1$–$C_{18}$)-heteroaryl, fluorine, hydroxyl, nitro, nitroso, CN, COOH, CHO, $PO_3H_2$, $SO_3H$, $SO_2R$, SOR, $NH_2$, NH-alkyl-($C_1$–$C_{18}$), N-alkyl$_2$-($C_1$–$C_{18}$), protected amine, $CF_3$, NHCO-alkyl-($C_1$–$C_4$), N-alkyl-($C_1$–$C_4$)-CO-alkyl-($C_1$–$C_4$), COO-alkyl-($C_1$–$C_{18}$), $CONH_2$, CO-alkyl-($C_1$–$C_{18}$), NHCOH, NHCOO-alkyl-($C_1$–$C_4$), CO-($C_1$–$C_{18}$)-aryl, COO-($C_1$–$C_{18}$)-aryl, CHCH-$CO_2$-alkyl-($C_1$–$C_{18}$), CHCHCO$_2$H, PO-phenyl$_2$, PO-alkyl$_2$-($C_1$–$C_4$), $(COO^-)_n(cation)^{n+}$, $(PO_3^{2-})_n(cation)_2^{n+}$, $(SO_3^-)_n(cation)^{n+}$ and/or $(O^-)_n(cation)^{n+}$, where the cation is an alkaline earth metal, alkali metal, $NR_2H_2$, $NR_3H$, $NRH_3$, $NR_4$, $NH_4$, $PR_2H_2$, $PR_3H$, $PRH_3$, $PR_4$ and/or $PH_4$ and where R, independently of one another, are identical or different and are ($C_1$–$C_{18}$)-aryl and/or ($C_1$–$C_{18}$)-alkyl, where optionally R1 to R4 among one another together form one or more aliphatic and/or aromatic rings and/or in which optionally R1, R2, R3 or R4 of one ring forms a bridge to R1, R2, R3 or R4 of the second ring and/or in which optionally the radicals R1 to R4 have the meanings given above and are substituted by at least one radical which has the meaning given above for R1 to R4, by converting 2-halopyridines of the formula (VII), 3-halopyridines of the formula (VIII) or 4-halopyridines of the formula (IX)

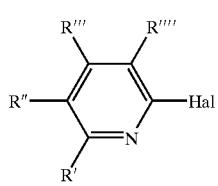

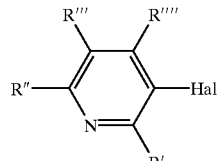

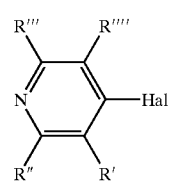

in which R', R'', R''' and R'''' have the meanings given above for R1 to R4 and in which Hal means chlorine, bromine or iodine, in water in the presence of an alcohol, a base, a palladium catalyst and optionally one or more further solvents at a temperature of 0–200° C.

"Protected amine" means amines with protective groups, as described, for example, in Greene, Theodora W.; Wuts, Peter G. M. Protective Groups in Organic Synthesis, $2^{nd}$ Ed. 1991, Publisher: John Wiley and Sons, Inc., New York, N.Y. Reference is made expressly to this publication; by virtue of being cited, it forms part of the description.

In the preparation of these symmetrical bipyridyls, a halopyridine of the formula (VII) produces the symmetrical 2,2'-bipyridyls of the formula (IV), the halopyridine of the formula (VIII) produces the symmetrical 3,3'-bipyridyls of the formula (V), and the halopyridine of the formula (IX) produces the symmetrical 4,4'-bipyridyls of the formula (VI).

Preferably:

R1 to R4, independently of one another, are hydrogen, $C_1$–$C_8$-alkyl, alkoxy-($C_1$–$C_8$), acyloxy-($C_1$–$C_8$), aryloxy-($C_1$–$C_{18}$), ($C_1$–$C_{18}$)-aryl, ($C_1$–$C_{18}$)-heteroaryl, fluorine, hydroxyl, nitro, nitroso, CN, COOH, CHO, $PO_3H_2$, $SO_3H$, $SO_2R$, SOR, $NH_2$, NH-alkyl-($C_1$–$C_8$), N-alkyl$_2$-($C_1$–$C_8$), protected amine, $CF_3$, NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NHCOO-alkyl-($C_1$–$C_4$), CO-($C_1$–$C_{18}$)-aryl, COO-($C_1$–$C_{18}$)-aryl, CHCH-$CO_2$-alkyl-($C_1$–$C_8$), CHCHCO$_2$H, PO-phenyl$_2$, PO-alkyl$_2$-($C_1$–$C_4$), $(COO^-)_n(cation)^{n+}$, $(PO_3^{2-})_n(cation)_{2+}$, $(SO_3^-)_n(cation)^{n+}$ and/or $(O^-)_n(cation)^{n+}$, where the cation is Na, Li, K, Ca, Mg, $NR_3H$, $NR_4$, $NH_4$, $PR_3H$, $PR_4$ and/or $PH_4$ and where R, independently of one another, are identical or different and are ($C_1$–$C_{18}$)-aryl and/or ($C_1$–$C_{18}$)-alkyl and where at least one of the substituents of R1 to R4 is a non-inert substituent such as acyloxy-($C_1$–$C_8$), hydroxyl, COOH, $PO_3H_2$, $SO_3H$, $SO_2R$, $NH_2$, NH-alkyl-($C_1$–$C_8$), N-alkyl$_2$-($C_1$–$C_8$), protected non-inert amine, NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NHCOO-alkyl-($C_1$–$C_4$), COO-($C_{1-C18}$)-aryl, CHCH-$CO_2$-alkyl-($C_1$–$C_8$), CHCHCO$_2$H, $(COO^-)_n(cation)^{n+}$. $(PO_3^{2-})_n(cation)_2^{n+}$, $(SO_3^-)_n(cation)^{n+}$ and/or $(O^-)_n(cation)^{n+}$, where the cation is Na, Li, K, Ca, Mg, $NR_3H$, $NR_4$, $NH_4$, $PR_3H$, $PR_4$ and/or PH4 and where R, independently of one another, are identical or different and are ($C_1$–$C_{18}$)-aryl and/or ($C_1$–$C_{18}$)-alkyl, where optionally R1 to R4 among one another together form one or more aliphatic and/or aromatic rings, and/or in which optionally R1, R2, R3 or R4 of one ring forms a bridge to R1, R2, R3 or R4 of the second ring and/or in which optionally the radicals R1 to R4 have the meanings given above and are substituted by at least one radical which has the meaning given above for R1 to R4.

Non-inert substituents are regarded as those which react with at least one compound in the reaction medium, so that stable adducts or else the substituent as such can be changed. Thus, for example, a COOH group is to be regarded as non-inert since it spontaneously enters, in the reaction medium, into an acid-base reaction, and also a COONa group since, being a basic compound, it can react with the acid which forms, which is usually scavenged by additions of base.

Particularly preferably:

R1 to R4, independently of one another, are hydrogen, methyl, ethyl, tert-butyl, isopropyl, methoxy, acetoxy, trifluoroacetoxy, trifluoromethyl, O-phenyl, phenyl, fluorine, OH, nitroso, $NO_2$, CN, COOH, CHO, $PO_3H_2$, $SO_3H$, $NH_2$, NH-alkyl-$(C_1-C_8)$, N-alkyl$_2$-$(C_1-C_8)$, NHCO-alkyl-$(C_1-C_4)$, N-alkyl-$(C_1-C_4)$-CO-alkyl-$(C_1-C_4)$, COO-alkyl-$(C_1-C_8)$, $CONH_2$, CO-alkyl-$(C_1-C_8)$, NHCOH, NHCOO-alkyl-$(C_1-C_4)$, CO-phenyl, COO-phenyl, CHCH—$CO_2$-alkyl-$(C_1-C_8)$, $CHCHCO_2H$, PO-phenyl$_2$, PO-alkyl$_2$-$(C_1-C_4)$, $(COO^-)_n(cation)^{n+}$, $(PO_3^{2-})_n(cation)_2^{n+}$, $(SO_3^-)_n(cation)^{n+}$ and/or $(O^-)_n(cation)^{n+}$, where the cation is Na, Li, K, $NR_3H$, $NR_4$, $PR_3H$ and/or $PR_4$ and where R, independently of one another, are identical or different and are $(C_1-C_{18})$-aryl and/or $(C_1-C_{18})$-alkyl and where at least one of the substituents of R1 to R4 is a non-inert substituent such as acetoxy, trifluoroacetoxy, OH, COOH, $PO_3H_2$, $SO_3H$, $NH_2$, NH-alkyl-$(C_1-C_8)$, N-alkyl$_2$-$(C_1-C_8)$, NHCO-alkyl-$(C_1-C_4)$, N-alkyl-$(C_1-C_4)$-CO-alkyl-$(C_1-C_4)$, COO-alkyl-$(C_1-C_8)$, $CONH_2$, CO-alkyl-$(C_1-C_8)$, NHCOH, NHCOO-alkyl-$(C_1-C_4)$, COO-phenyl, $CHCH-CO_2$-alkyl-$(C_1-C_8)$, $CHCHCO_2H$, $(COO^-)_n(cation)^{n+}$, $(PO_3^{2-})_n(cation)_2^{n+}$, $(SO_3^-)_n(cation)^{n+}$ and/or $(O^-)_n(cation)^{n+}$, where the cation is Na, Li, K, $NR_3H$, $NR_4$, $PR_3H$ and/or $PR_4$ and where R, independently of one another, are identical or different and are $(C1-C_{18})$-aryl and/or $(C_1-C_{18})$-alkyl, where optionally R1 to R4 among one another together form one or more aliphatic and/or aromatic rings and/or in which optionally R1, R2, R3 or R4 of one ring forms a bridge to R1, R2, R3 or R4 of the second ring and/or in which optionally the radicals R1 to R4 have the meanings given above and are substituted by at least one radical which has the meaning given above for R1 to R4.

Very particularly preferably:

R1 to R4, independently of one another, are hydrogen, methyl, ethyl, isopropyl, methoxy, acetoxy, trifluoroacetoxy, trifluoromethyl, trichloromethyl, O-phenyl, phenyl, fluorine, OH, nitroso, $NO_2$, CN, COOH, CHO, $PO_3H_2$, $SO_3H$, $NH_2$, NH-alkyl-$(C_1-C_8)$, N-alkyl$_2$-$(C_1-C_8)$, NHCO-alkyl-$(C_1-C_4)$, N-alkyl-$(C_1-C_4)$-CO-alkyl-$(C_1-C_4)$, $CONH_2$, CO-alkyl-$(C_1-C_8)$, NHCOH, CO-phenyl, $CHCHCO_2H$, PO-phenyl$_2$, PO-alkyl2-$(C_1-C_4)$, $(COO^-)_n(cation)^{n+}$, $(PO_3^{2-})_n(cation)_2^{n+}$, $(SO_3^-)_n(cation)^{n+}$ and/or $(O^-)_n(cation)^{n+}$, where the cation is Na, K, $NR_4$ and/or $PR_4$ and where R, independently of one another, are identical or different and are $(C_1-C_{18})$-aryl and/or $(C_1-C_{18})$-alkyl and where at least one of the substituents of R1 to R4 is a non-inert substituent such as OH, COOH, $PO_3H_2$ or $SO_3H$, $(COO^-)_n(cation)^{n+}$, $(PO_3^{2-})_n(cation)_2^{n+}$, $(SO_3^-)_n(cation)^{n+}$ and/or $(O^-)_n(cation)^{n+}$, where the cation is Na, K, $NR_4$ and/or $PR_4$ and where R, independently of one another, are identical or different and are $(C_1-C_{18})$-aryl and/or $(C_1-C_{18})$-alkyl, where optionally R1 to R4 among one another together form one or more aliphatic and/or aromatic rings and/or in which optionally R1, R2, R3 or R4 of one ring forms a bridge to R1, R2, R3 or R4 of the second ring and/or in which optionally the radicals R1 to R4 have the meanings given above and are substituted by at least one radical which has the meaning given above for R1 to R4.

It is also possible to use the salts of the halopyridines for the conversion. Thus, in particular an alkali metal salt, e.g. the sodium salt, of a halopyridinecarboxylic acid or a hydrochloride of a halopyridine can be used.

The radicals R', R'', R''' and/or R'''' can optionally be substituted. Suitable substituents are the radicals R1 to R4 themselves, in particular the non-inert substituents, such as OH, COOH, $PO_3H_2$ and/or $SO_3H$.

If two or more different monohalopyridines are used, unsymmetrically coupled bipyridyls are also produced in addition to the symmetrical bipyridyls.

Surprisingly and in contrast to the results to be expected in accordance with the prior art, it has been found that halopyridines containing non-inert substituents can be converted particularly well in water in the presence of an alcohol, such as, for example, methanol, a base, such as, for example, sodium hydroxide, a palladium catalyst and optionally at least one further water-miscible or water-immiscible solvent, but also without further additives, such as, for example, reducing compounds, such as hydrazine or hydroxylamine, at temperatures of 0–200° C.

In the case of the particularly preferred halopyridyls, a high water content in the reaction medium (>35%) favors the formation of the bipyridyl, which was not to be expected according to the prior art. Preference is given to using a water content in the reaction medium of at least 40%, in particular of at least 50%, for the formation of the bipyridyls.

As palladium catalyst, the use of unsupported and, preferably, of supported palladium has proven successful. Suitable supports are the supports customarily used for palladium, in particular activated carbon, metal oxides and/or metal salts, such as, for example, sulfates and/or carbonates of the metals of main groups 2 to 3 and/or of subgroups 1 to 3, such as, for example, aluminum oxide, barium sulfate, calcium carbonate and/or silicon dioxide and, particularly preferably, activated carbon. The supports can also be used in the process according to the invention in mixed form. Suitable as palladium catalysts are both metallic palladium, and also a palladium compound, optionally in combination with one another.

Surprisingly, it has been found that the loading of the palladium on the support, for the same total amount of palladium used, is of considerable importance for the reaction rate. For example, it has been found that 30% by weight of palladium on activated carbon reacts many times more quickly than the same amount of palladium as 5% by weight of palladium on activated carbon. In particular, the loading of the palladium on the support is at least 5% by weight, preferably at least 10% by weight, particularly preferably at least 20% by weight.

The process of the invention is preferably notable for the fact that the palladium catalyst, in each case calculated on the basis of palladium metal, is used in an amount of from 0.0001 to 10 mol %, preferably in an amount of from 0.1 to 5 mol %, based on halopyridine. If more palladium is used, the reaction rate increases accordingly, giving a higher space-time yield.

Particularly in a process in which the palladium catalyst is recovered by simple separation and re-used, the use of large amounts of palladium is therefore advantageous.

The alcohol serves primarily as reducing agent in the reaction and can be further oxidized to give the secondary products aldehyde or ketone, carboxylic acid and/or carbon dioxide or carbonic acid. The aldehydes or ketones which arise in the reaction can further react in the alkaline reaction medium in the sense of an aldol reaction. The alcohols used are therefore preferably alcohols which, following oxidation to the aldehyde or ketone, are unable or are able only with difficulty to participate in an aldol reaction. Methanol and/or ethylene glycol have proven particularly suitable for the process according to the invention.

Bases which can be used are, for example, salts of weak and strong acids. In particular, it is possible to use alkali metal salts and/or alkaline earth metal salts, preferably alkali metal hydroxides, alkaline earth metal hydroxides, alkali metal carbonates, alkaline earth carbonates, alkali metal hydrogencarbonates, alkaline earth metal hydrogencarbonates, alkali metal acetates and/or alkaline earth metal acetates, particularly preferably sodium hydroxide and/or potassium hydroxide.

The reaction is carried out at a temperature of from 0 to 200° C., in particular 10 to 180° C, preferably 20 to 150° C. and particularly preferably 50 to 120° C. The reaction according to the invention is preferably carried out at 0.1 to 2 MPa, in particular at 0.1 to 0.5 MPa. The increased pressure essentially serves to increase the boiling point of the solvent used in order to enable the optimum reaction temperature to be set. The reaction product preferably comprises 2,2'-bipyridyl-4,4'-dicarboxylic acid.

If dihalopyridines, such as, for example, 2,6-dichloroisonicotinic acid are used, as well as the bipyridyls, oligo- and polypyridyls also form, which usually precipitate out of the solution as solid. During the reaction, the dehalogenated products also usually form as byproducts. The chain length of the oligo- and polypyridyls is determined by the ratio of the reaction rates of the reductive dimerization to the dehalogenation. Transference of the process according to the invention to dihalopyridyls, which for the example 2,6-dichloroisonicotinic acid, follows the reaction equation

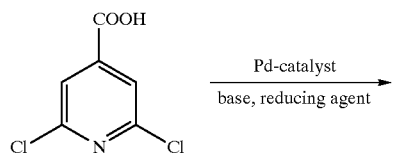

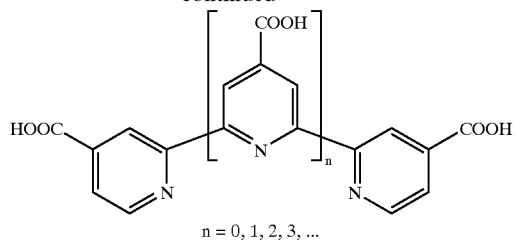

n = 0, 1, 2, 3, ...

can therefore be used for the synthesis of mixtures of bi-, oligo- and polypyridyls.

The reaction product of the process according to the invention is preferably reacted with at least one transition metal from subgroup 7 and/or 8, preferably manganese, and/or a noble metal, in particular ruthenium, and/or compounds thereof to give at least one bipyridyl metal complex. These transition metal complexes are highly suitable as sensitizing dyes for dye-sensitized solar cells. Ruthenium complexes in particular, because of their light-absorption and electron-injection properties, have proven particularly suitable in semiconductors such as $TiO_2$. Particularly suitable examples which may be mentioned are the compounds cis-$X_2$bis(2,2'-bipyridyl-4,4'-dicarboxylate)ruthenium(II) where X =Cl, Br, I, CN or SCN. Such compounds can, for example, be obtained from the conversion of water- or methanol-soluble bipyridyl compounds or their salts with metal salts.

Such a reaction product is therefore highly suitable for use in photovoltaic or photoelectrochemical cells, in particular in solar cells, or for photo-induced electrolysis.

The examples below serve to illustrate the process without limiting it thereto.

EXAMPLES

Example 1

25 g of 6-chloronicotinic acid and 14 g of sodium hydroxide are dissolved in a mixture of 100 ml of water and 80 ml of ethylene glycol. Following the addition of 0.56 g of palladium (30% by weight on activated carbon; corresponds to an addition of 168 mg of pure palladium) as catalyst, the mixture is stirred for 5 h at 80–85° C. at 0.1 MPa. The catalyst is then filtered off. Following acidification to pH 1 using hydrochloric acid, the product, 2,2'-bipyridyl-5,5'-dicarboxylic acid, precipitates out as a white solid. This gives 15.7 g (81% yield). According to $^1$H NMR, the crude product has a purity of about 95%. CAS Registry Number: 1802-30-8.

$^1$H NMR (400 MHz, DMSO): d=13.51 (s broad, 2H); 9.20 (dd, J=2.1, 0.8 Hz, 2H); 8.57 (dd, J=8.2, 0.8 Hz, 2H); 8.45 (dd, J=8.2, 2.1 Hz, 2H). $^{13}$C NMR (100 MHz, DMSO): d=165.92, 157.29, 150.25 (CH), 138.38 (CH), 127.09, 121.05 (CH).

Example 2

25 g of 6-chloronicotinic acid and 14 g of sodium hydroxide are dissolved in a mixture of 100 ml of water and 80 ml of methanol. Following the addition of 5 g of palladium (10% by weight on activated carbon) as catalyst, the mixture is stirred for 24 h at 80–85° C. at 0.1 MPa. The catalyst is then filtered off. Following acidification to pH 1 using hydrochloric acid, the product, 2,2'-bipyridyl-5,5'-dicarboxylic acid, precipitates out as a white solid. This gives 16.3 g (84% yield). According to $^1$H NMR, the crude product has a purity of about 95%.

$^1$H NMR (400 MHz, DMSO): corresponds to Example 1.

Example 3

25 g of 6-chloronicotinic acid and 14 g of sodium hydroxide are dissolved in a mixture of 100 ml of water and 80 ml of methanol. Following the addition of 10 g of palladium (5% by weight on activated carbon) as catalyst, the mixture is stirred for 30 h at 80–85° C. at 0.1 MPa. The catalyst is then filtered off. Following acidification to pH 1 using hydrochloric acid, the product, 2,2'-bipyridyl-5,5'-dicarboxylic acid, precipitates out as a white solid. This gives 15.3 g (79% yield). According to $^1$H NMR, the crude product has a purity of about 95%.

$^1$H NMR (400 MHz, DMSO): corresponds to Example 1.

Example 4

9.50 g of 2-chloronicotinic acid and 5.30 g of sodium hydroxide are dissolved in a mixture of 40 ml of water and 40 ml of methanol. Following the addition of 4 g of palladium (5% by weight on activated carbon) as catalyst, the mixture is stirred for 30 h at 80–85° C. at 0.1 MPa. The catalyst is then filtered off. Following acidification to pH 1 using hydrochloric acid, the product, 2,2'-bipyridyl-3,3'-dicarboxylic acid, precipitates out as a white solid. This gives 3.5 g (48% yield). According to $^1$H NMR, the crude product has a purity of about 95%. CAS Registry Number: 4433-01-6.

$^1$H NMR (360 MHz, DMSO): d=13.6 (s broad, 2H); 8.51 (dd, J=2, 5 Hz, 2H); 8.17 (dd, J=2,8 Hz, 2H); 7.49 (dd, J =5,8Hz, 2H). $^{13}$C NMR (90 MHz, DMSO): d=165.76, 157.53, 150.14 (CH), 138.08 (CH), 127.24, 121.00 (CH).

Example 5

5.00 g of 2-chloroisonicotinic acid and 2.80 g of sodium hydroxide are dissolved in a mixture of 20 ml of water and 16 ml of methanol. Following the addition of 1.02 g of palladium (10% by weight on activated carbon) as catalyst, the mixture is stirred for 6 h at 80–85° C. at 0.1 MPa. The catalyst is then filtered off. Following acidification to pH 1 using hydrochloric acid, the product, 2,2'-bipyridyl-4,4'-dicarboxylic acid, precipitates out as a white solid. This gives 3.3 g (85% yield). According to $^1$H NMR, the crude product has a purity of about 90%. CAS Registry Number: 6813-38-3. $^1$H NMR (300 MHz, DMSO): d=13.6 (s broad, 2H); 8.80 (m, 2H); 8.31 (m, 2H) ;7.84 (m, 2H).

Example 6

2.55 g of 6-chloro-2-picoline and 1.00 g of sodium hydroxide are stirred into a mixture of 15 ml of water and 8 ml of methanol. Following the addition of 1.3 g of palladium (5% by weight on activated carbon) as catalyst, the mixture is stirred for 20 h at 80–85° C. at 0.1 MPa. The mixture is then diluted with 20 ml of methanol and the catalyst is filtered off. After the methanol has been stripped off, the product, 6,6'-dimethyl-2,2'-bipyridyl, crystallizes in the form of lamellar crystals. This gives 1.10 g (58% yield). According to $^1$H NMR, the crude product has a purity of >98%. CAS Registry Number: 4411-80-7.

$^1$H NMR (300 MHz, DMSO): d=8.18 (d, J=8 Hz, 2H) ; 7.81 (t, J=8 Hz, 2H) ; 7.29 (d, J=8 Hz, 2H); 2.56 (s, 6H).

Example 7

5.00 g of 5-chloro-2-hydroxypyridine and 4.00 g of sodium hydroxide are dissolved in a mixture of 30 ml of water and 16 ml of methanol. Following the addition of 2.5 g of palladium (5% by weight on activated carbon) as catalyst, the mixture is stirred for 20 h at 80–85° C. at 0.1 MPa. The mixture is then diluted with 20 ml of methanol and the catalyst is filtered off. After the methanol has been stripped off, the mixture is acidified to pH 3 to 4 using hydrochloric acid. The product, 6,6'-dihydroxy-3,3'-bipyridyl (3,3'-bipyridine-6,6'-diol), precipitates out as a white solid. This gives 1.74 g (48% yield). According to $^1$H NMR, the crude product has a purity of >98%. CAS Registry Number: 142929-10-0.

$^1$H NMR (360 MHz, DMSO): d=11.38 (s broad, 2H); 7.61 (dd, J=3, 10 Hz, 2H) ; 7.50 (t, J=3Hz, 2H) ; 6.37 (d, J=3 Hz, 2H).

Example 8

5.00 g of 6-chloro-2-hydroxypyridine and 4.00 g of sodium hydroxide are 10 dissolved in a mixture of 30 ml of water and 16 ml of methanol. Following the addition of 2.5 g of palladium (5% by weight on activated carbon) as catalyst, the mixture is stirred for 20 h at 80–85° C. at 0.1 MPa. The mixture is then diluted with 20 ml of methanol and the catalyst is filtered off. The catalyst is dried under reduced pressure at 80° C. and re-used in Example 9. After the methanol has been stripped off, the mixture is acidified to pH 3 to 4 using hydrochloric acid. The product, 6,6'-dihydroxy-2,2'-bipyridyl (2,2'-bipyridine-6,6'-diol), precipitates out as a white solid. This gives 1.45 g (40% yield). According to H NMR, the crude product has a purity of >98%. CAS Registry Number: 103505-54-0.

$^1$H NMR (360 MHz, DMSO): d=10.74 (s broad, 2H); 7.63 (dd, J =7, 9 Hz, 2H) ; 7.21 (t, J=7 Hz, 2H); 6.56 (d, J=9 Hz, 2H).

Example 9 (recycling the catalyst)

5.00 g of 6-chloro-2-hydroxypyridine and 4.00 g of sodium hydroxide are dissolved in a mixture of 30 ml of water and 16 ml of methanol. Following the addition of the catalyst separated off in Example 8, the mixture is stirred for 20 h at 80–85° C. at 0.1 MPa. The mixture is then diluted with 20 ml of methanol and the catalyst is filtered off. After the methanol has been stripped off, the mixture is acidified to pH 3 to 4 using hydrochloric acid. The product, 6,6'-dihydroxy-2,2'-bipyridyl (2,2'-bipyridine-6,6'-diol), precipitates out as a white solid. This gives 2.2 g (61% yield). According to $^1$H NMR, the crude product has a purity of >98%.

$^1$H NMR (360 MHz, DMSO): corresponds to Example 7.

Example 10

5.00 g of 2-chloroquinoline and 1.80 g of sodium hydroxide are dissolved in a mixture of 20 ml of water and 16 ml of methanol. Following the addition of 1.5 g of palladium (10% by weight on activated carbon) as catalyst, the mixture is stirred for 24 h at 80–85° C. at 0.1 MPa. Then, following cooling, the catalyst and the precipitated product are filtered off. Extraction of the catalyst gives 1.7 g of 2,2'-biquinoline (43% yield). According to $^1$H NMR, the crude product has a purity of about 98%. CAS Registry Number: 119-91-5.

$^1$H NMR (300 MHz, DMSO): d=8.81 (d, J=9 Hz, 2H); 8.58 (d, J=9 Hz, 2H); 8.20 (d broad, J=9 Hz, 2H); 8.08 (d broad, J=8 Hz, 2H); 7.86 (ddd, J 2, 7, 9 Hz, 2H), 7.86 (ddd, J=1, 7, 8 Hz, 2H).

What is claimed is:

1. A process for the preparation of symmetrical 2,2'-bipyridyls of the formula (IV), symmetrical 3,3'-bipyridyls of the formula (V) or symmetrical 4,4'-bipyridyls of the formula (VI),

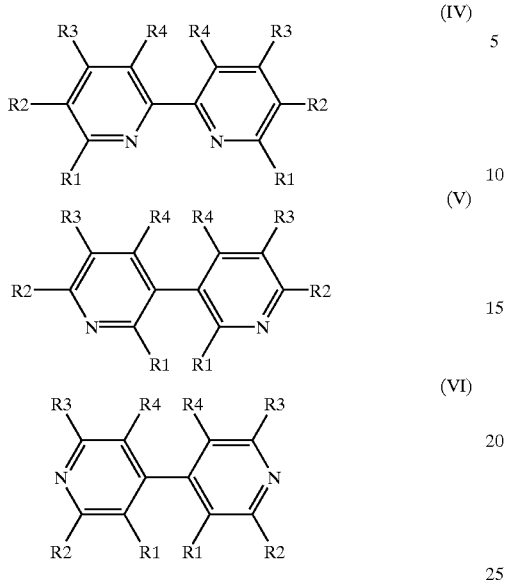

(IV)

(V)

(VI)

in which
R1 to R4, independently of one another, are identical or different and are:
hydrogen, $C_1$–$C_8$-alkyl, alkoxy-($C_1$–$C_8$), acyloxy-($C_1$–$C_8$), aryloxy-($C_1$–$C_{18}$), an aryl containing up to 18 carbon atoms, heteroaryl containing up to 18 carbon atoms, fluorine, hydroxyl, nitro, nitroso, CN, COOH, CHO, $PO_3H_2$, $SO_3H$, $SO_2R$, SOR, $NH_2$, NH-alkyl-($C_1$–$C_8$), N-alkyl$_2$-($C_1$–$C_8$), protected amine $CF_3$, NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NHCOO-alkyl-($C_1$–$C_4$), CO-aryl containing up to 18 carbon atoms, COO-aryl containing up to 18 carbon atoms, CHCH-$CO_2$-alkyl-($C_1$–$C_8$), $CHCHCO_2H$, PO-phenyl$_2$, PO-alkyl$_2$-($C_1$–$C_4$), $(COO^-)_n$(cation)$^{n+}$, $(PO_3^{2-})_n$(cation)$_2^{n+}$,
$(SO_{3-})_n$(cation)$^{n+}$ or $(O^-)_n$(cation)$^{n+}$,
where the cation is Na, Li, K, Ca, Mg, $NR_3H$, $NR_4$, $NH_4$, $PR_3H$, $PR_4$ or $PH_4$ n is the number of anions and the number of the positive charge on the cation and n and n+ are the same number, and
where R, independently of one another, are identical or different and are an aryl containing up to 18 carbon atoms or ($C_1$–$C_{18}$)-alkyl,
and where at least one of the substituents of R1 to R4 is a substituent selected from the group consisting of acyloxy-($C_1$–$C_8$), hydroxyl, COOH, $PO_3H_2$, $SO_3H$, $SO_2R$, $NH_2$, NH-alkyl-($C_1$–$C_8$), N-alkyl$_2$-($C_1$–$C_8$), protected non-inert amine, NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NHCOO-alkyl-($C_1$–$C_4$), COO-aryl containing up to 18 carbon atoms, CHCH-$CO_2$-alkyl-($C_1$–$C_8$), $CHCHCO_2H$, $(COO^-)_n$(cation)$^{n+}$, $(PO_3^{2-})_n$(cation)$_2^{n+}$, $(SO_3^-)_n$(cation)$^{n+}$ and $(O^-)_n$(cation)$^{n+}$,
where the cation is Na, Li, K, Ca, Mg, $NR_3H$, $NR_4$, $NH_4$, $PR_3H$, $PR_4$ or $PH_4$ and n is the number of anions and the number of the positive charge on the cation and n and n+ are the same number, and
where R, independently of one another, a;-e identical or different and are an aryl containing up to 18 carbon atoms or ($C_1$–$C_{18}$)-alkyl, where optionally R1 to R4 among one another together form one or more aliphatic or aromatic rings, and in which optionally R1, R2, R3 or R4 of one ring forms a bridge to R1, R2, R3 or R4 of the second ring
and in which optionally the radicals R1 to R4 have the meanings given above and are substituted by at least one radical which has the meaning given above for R1 to R4,
2-halopyridines of the formula (VII), 3-halopyridines of the formula (VIII) or 4-halopyridines of the formula (IX) are reacted,

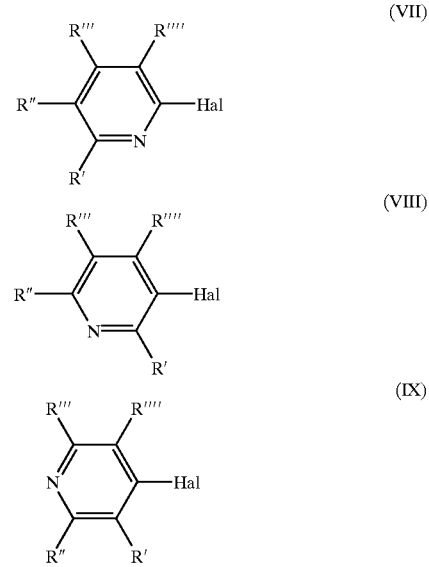

(VII)

(VIII)

(IX)

in which R', R'', R''' and R'''' have the meanings given above for RI to R4 and in which Hal means chlorine, bromine or iodine,
in water in the presence of an alcohol, a base, a palladium catalyst and optionally one or more further solvents at a temperature of 0–200° C.

2. The process as claimed in claim 1, wherein R1 to R4, independently of one another, are identical or different and are: hydrogen, methyl, ethyl, tert-butyl, isopropyl, methoxy, acetoxy, trifluoroacetoxy, trifluoromethyl, O-phenyl, phenyl, fluorine, OH, nitroso, $NO_2$, CN, COOH, CHO, $PO_3H_2$, $SO_3H$, $NH_2$, NH-alkyl-($C_1$–$C_8$), N-alkyl$_2$-($C_1$–$C_8$), NHCO-alkyl-($C_1$–$C_4$). N-alkyl-($C_1$–$C_4$)-CO-alkyl-($C_1$–$C_4$), COO-alkyl-($C_1$–$C_8$), $CONH_2$, CO-alkyl-($C_1$–$C_8$), NHCOH, NHCOO-alkyl-($C_1$–$C_4$), CO-phenyl, COO-phenyl, CHCH-$CO_2$-alkyl-($C_1$–$C_8$), $CHCHCO_2H$, PO-phenyl$_2$, PO-alkyl$_2$-($C_1$–$C_4$), $(COO^-)_n$(cation)$^{n+}$, $(PO_3^{2-})_n$(cation)$_2^{n+}$, $(SO_3^-)_n$(cation)$^{n+}$ or $(O^-)_n$(cation)$^{n+}$,
where the cation is Na, Li, K, $NR_3H$, $NR_4$, $PR_3H$ or $PR_4$ and
where R, independently of one another, are identical or different and are an aryl containing up to 18 carbon atoms or ($C_1$–$C_{18}$)-alkyl
and where at least one of the substituents of R1 to R4 is a substituent selected from the group consisting of acetoxy, trifluoroacetoxy, OH, COOH, $PO_3H_2$, $SO_3H$, $NH_2$, NH-alkyl-($C_1$–$C_8$), N-alkyl$_2$-($C_1$–$C_8$), NHCO-alkyl-($C_1$–$C_4$), N-alkyl-($C_1$–$C_4$)-CO-alkyl-($C_1$–$C_4$), COO-alkyl-($C_1$–$C_8$), $CONH_2$, CO-alkyl-($C_1$–$C_8$). NHCOH, NHCOO-alkyl-($C_1$–$C_4$), COO-phenyl, CHCH-$CO_2$-alkyl-($C_1$–$C_8$), $CHCHCO_2H$, $(COO^-)_n$(cation)$^{n+}$, $(PO_3^{2-})_n$(cation)$_2^{n+}$, $(SO_3^-)_n$(cation)$^{n+}$ and $(O^-)_n(cation)^{n+}$, where the cation is Na, Li, K, $NR_3H$, $NR_4$, $PR_3H$ or $PR_4$ and where R are identical or different and are an aryl containing up to 18 carbon atoms or $(C_1-C_{18})$-alkyl, where optionally R1 to R4 among one another together form one or more aliphatic or aromatic rings, and in which optionally R1, R2, R3 or R4 of one ring forms a bridge to R1, R2, R3 or R4 of the second ring, and in which optionally the radicals R1 to R4 have the meanings given above and are substituted by at least one radical which has the meaning given above for R1 to R4.

3. The process as claimed in claim 1, wherein R1 to R4, independently of one another, are identical or different and are: hydrogen, methyl, ethyl, isopropyl, methoxy, acetoxy, trifluoroacetoxy, trifluoromethyl, trichloromethyl, O-phenyl, phenyl, fluorine, OH, nitroso, $NO_2$, CN, COOH, CHO, $PO_3H_2$, $SO_3H$, $NH_2$, NH-alkyl-$(C_1-C_8)$, N-alkyl$_2$-$(C_1-C_8)$, NHCO-alkyl-$(C_1-C_4)$, N-alkyl alkyl-$(C_1-C_4)$, $CONH_2$, CO-alkyl-$(C_1-C_8)$, NHCOH, CO-phenyl, $CHCHCO_2H$, PO-phenyl$_2$, PO-alkyl$_2$-$(C_1-C_4)$, $(COO^-)_n(cation)^{n+}$, $(PO_3^{2-})_n(cation)_2^{n+}$, $(SO_3^-)_n(cation)^{n+}$ or $(O^-)_n(cation)^{n+}$, where the cation is Na, K, $NR_4$ or $PR_4$ and where R, independently of one another, are identical or different and are an aryl containing up to 18 carbon atoms or $(C_1-C_{18})$-alkyl and where at least one of the substituents of R1 to R4 is a substituent selected from the group consisting of OH, COOH, $PO_3H_2$ or $SO_3H$, $(COO^-)_n(cation)^{n+}$, $(PO_3^{2-})_n(cation)_2^{n+}$, $(SO_3^-)_n(cation)^{n+}$ and $(O^-)_n(cation)^{n+}$ where the cation is Na, K, $NR_4$ or $PR_4$ and where R are identical or different and are an aryl containing up to 18 carbon atoms or $(C_1-C_{18})$-alkyl, where optionally at least one R1 to R4 among one another together form one or more aliphatic or aromatic rings, and in which optionally R1, R2, R3 or R4 of one ring forms a bridge to R1, R2, R3 or R4 of the second ring, and in which optionally the radicals R1 to R4 have the meanings given above and are substituted by at least one radical which has the meaning given above for R1 to R4.

4. The process as claimed in claim 1, wherein the salts of the halopyridines are used for the conversion of a halopyridinecarboxylic acid or a hydrochloride of a halopyridine.

5. The process as claimed in claim 1, where at least one of the radicals R', R'', R''' or of R'''' are substituted by the radicals R1 to R4.

6. The process as claimed in claim 1, wherein, if two or more different monohalopyridines are used, unsymmetrically coupled bipyridyls are produced in addition to the symmetrical bipyridyls.

7. The process as claimed in claim 1, wherein halopyridines containing non-inert substituents are converted in water in the presence of an alcohol, a base, a palladium catalyst and optionally at least one further water-miscible or water-immiscible solvent, but also without hydrazine or hydroxylamine, at temperatures of 0–200° C.

8. The process as claimed in claim 1, wherein, if halopyridyls are used, a water content in the reaction medium of at least 35% is used.

9. The process as claimed in claim 1, wherein the palladium catalyst used is an unsupported or supported palladium, it being possible to use a metallic palladium, or a palladium compound, optionally in combination with one another.

10. The process as claimed in claim 9, wherein the support used for palladium is activated carbon, metal oxides or metal salts.

11. The process as claimed in claim 9, wherein the loading of the palladium on the support is at least 5% by weight.

12. The process as claimed in claim 9, wherein the palladium catalyst, in each case calculated on the basis of palladium metal, is used in an amount of from 0.0001 to 10 mol % based on halopyridine.

13. The process as claimed in claim 1, wherein the alcohol used is one which, following oxidation to the aldehyde or ketone, is unable or is able only with difficulty to participate in an aldol reaction.

14. The process as claimed in claim 1, wherein the base used is a salt of weak or strong acid.

15. The process as claimed in claim 1, wherein the reaction is carried out at a temperature of from 0 to 200° C. and at 0.1 to 2 Mpa.

16. The process as claimed in claim 1, wherein the reaction product comprises 2,2'-bipyridyl-4,4'-dicarboxylic acid.

17. The process as claimed in claim 1, wherein the reaction product is reacted with a transition metal from subgroup 7 or 8 or at least one noble metal, to give at least one bipyridyl metal complex.

18. The process as claimed in claim 4, wherein the salts of the halopyridines are used for the conversion of a alkali metal salt of a halopyridinecarboxylic acid or hydrochloride of a halopyridine.

19. The process as claimed in claim 18, wherein the alkali metal salt is a sodium salt.

20. The process as claimed in claim 7, wherein the halopyridines containing the non-inert substituents are converted into water in the presence of methanol, sodium hydroxide, a palladium catalyst and optionally at least one further water-miscible or water-immiscible solvent.

21. The process as claimed in claim 10, wherein the support used for palladium is activated carbon, metal oxides, metal salts selected from group consisting of sulfate and carbonate of the metals of the main groups 2 to 3 and subgroups 1 to 3.

22. The process as claimed in claim 21, wherein the support is aluminum oxide, barium sulfate, calcium carbonate, silicon dioxide or activated carbon.

23. The process as claimed in claim 11, wherein the loading of the palladium on the support is at least 10% by weight and the palladium catalyst in each case calculated on the basis of palladium metal, is used in an amount of from 0.1 to 5 mol % based on the halopyridine.

24. The process as claimed in claim 23, wherein the loading of the palladium on the support is at least 20% by weight.

25. The process as claimed in claim 14, wherein the base is an alkali metal salt or an alkaline earth metal salt.

26. The process as claimed in claim 14, wherein the base is an alkali metal hydroxide, an alkaline earth metal hydroxide, alkali metal carbonate, alkaline earth metal carbonate, alkali metal hydrogencarbonate, alkaline earth metal hydrogencarbonate, alkali metal acetate, earth metal acetate, sodium hydroxide or potassium hydroxide.

27. The process as claimed in claim 14, wherein the base is sodium hydroxide or potassium hydroxide and the process is carried out from 10 to 180° C. at 0.1 to 0.5 MPa.

28. The process as claimed in claim 27, wherein the reaction is carried out at a temperature from 20 to 150° C.

29. The process as claimed in claim 28, wherein the process is carried out at a temperature of from 50 to 120° C.

30. The process as claimed in claim 17, wherein the reaction product is reacted with magnesium or ruthenium or compounds thereof to give at least on bipyridyl complex.

* * * * *

UNITED STATES PATENT AND TRADEMARK OFFICE
CERTIFICATE OF CORRECTION

PATENT NO.   : 6,500,956 B1
DATED        : December 31, 2002
INVENTOR(S)  : Holger Geissler et al.

It is certified that error appears in the above-identified patent and that said Letters Patent is hereby corrected as shown below:

Title page,
Item [54], Title, delete "BIPYRIDYL" and insert -- DIPYRIDYL --.

Column 13,
Line 65, delete "a;-e" and insert -- are --.

Column 14,
Line 37, delete "RI" and insert -- R1 --.

Column 15,
Line 19, delete "N-alkyl alkyl-$(C_1-C_4)$" and insert -- N-alkyl -$(C_1-C_4)$-CO-alkyl-$(C_1-C_4)$ --.

Signed and Sealed this

Seventeenth Day of June, 2003

JAMES E. ROGAN
*Director of the United States Patent and Trademark Office*